United States Patent
Wang et al.

(10) Patent No.: US 6,892,732 B2
(45) Date of Patent: May 17, 2005

(54) CONDOM COATED WITH LACTIC ACID BACTERIA CONTAINED COMPOSITION

(75) Inventors: Chih-Hong Wang, Taipei (TW); Hsin-Chung Chen, Taipei (TW); Yu-Shen Cheng, Taipei (TW)

(73) Assignee: Bioleader Technology Corp., Taipei (TW)

( * ) Notice: Subject to any disclaimer, the term of this patent is extended or adjusted under 35 U.S.C. 154(b) by 493 days.

(21) Appl. No.: 10/325,949

(22) Filed: Dec. 23, 2002

(65) Prior Publication Data

US 2004/0118408 A1 Jun. 24, 2004

(51) Int. Cl.$^7$ .................................................. A61F 6/04
(52) U.S. Cl. ...................................... 128/844; 128/918
(58) Field of Search ............................. 128/842, 844, 128/918; 604/347–353

(56) References Cited

U.S. PATENT DOCUMENTS 5,565,197 A * 10/1996 Allen .......................... 424/94.4
5,718,896 A * 2/1998 Allen .......................... 424/94.4
6,458,346 B1 * 10/2002 Howett ...................... 424/78.07

* cited by examiner

Primary Examiner—Michael A. Brown
(74) Attorney, Agent, or Firm—Rosenberg, Klein & Lee

(57) ABSTRACT

The present invention is a condom coated with lactic acid bacteria contained composition, which has not only provided the contraceptive effect and the prevention of sexually transmitted diseases transmission but also helped to establish, maintain and reestablish a non-pathogenic, natural or genetically modified intra-vaginal bacterial flora action in vagina. The lactic acid bacteria can be genetically modified and natural lactic acid bacteria such as spreads from mammal intestinal and vaginal tract. A condom is coated with composition containing powder form or other type of lactic acid bacteria such as cream, foam, micro-bead or micro-encapsulated form, which contains as its ingredients at least one species of viable lactic acid bacteria, and optionally with a lubricant. The risk of pathogenic microbial and viral infection in vagina can be decreased or prevented and the vaginal environment can be maintained in a good condition without side effect by using a condom of the present invention.

16 Claims, 3 Drawing Sheets

CONDOM COATED WITH LACTIC ACID BACTERIA CONTAINED COMPOSITION

BACKGROUND OF THE INVENTION

1. Field of the Invention

The present invention relates to a condom coated with genetically modified or natural lactic acid bacteria contained composition, and to the beneficial effect, don human healthy and sexually transmitted disease prevention, by using the condom presented in this invention.

2. Description of the Prior Art

Microbicidal and spermicidal compositions have been widely used in the prior art in creams, foams, suppositories by themselves and also in conjunction with various mechanical contraceptive devices, primarily for the purpose of contraception. Nonoxynol 9, a spermicidal agent, has also been reported to have certain bactericidal action and capable of killing the human immunodeficiency virus (HIV) in the prior art. However, the use of spermicidal and bactericidal agent, such as nonoxynol 9, in condom or other vaginally inserted suppositories is not without problems inasmuch as there agents tend to destroy or diminish the healthy bacterial flora of the vagina, and cause for the woman a risk to develop other microbial infections, such as yeast infection.

The condom is the most effective and most frequently using contraceptive method. Using the condom also helps prevent sexually transmitting disease by interposing between the female and male, most importantly between the uterine cervix and the glands and orifice of the penis. However, the spermicidal agents and the latex material of the condoms can erode the mucosa if used too frequently, and even with infrequent use, can disrupt the protection of vaginal healthy bacterial flora. Although the prior art has recognized the need to maintain or reestablish a healthy intra-vaginal bacterial flora, the only solution provide to this problem in the prior art was in the form of douches or other types of vaginal cleaning systems which contained a colony of *Lactobacillus acidophilus*. These douches or other vaginal cleaning systems are inconvenient, and they also contribute nothing to contraception, nor do they protect against transmission of sexually transmitted diseases during heterosexually intercourse.

Lactic acid bacteria, such as *Lactobacillus casei* and *Lactobacillus fermentum*, have been reported to have healthy action in vagina is not only in the natural form but also can be genetically modified. The prior art has indicated that a lactic acid bacteria can be genetically modified to express the polypeptide or carbohydrate moiety on the bacterial surface or in the intracellular environment, which have the ability to bind, inactive or remove the pathogenic microbial from vagina and also have the ability to act on the immunity reaction of human to against the viral infection in vagina, such as human papillomavirus (HPV).

The present invention provides a condom coated with lactic acid bacteria contained compositions which has not only provided contraceptive effect and protection against transmission of sexually transmitted diseases but also helped to establish, maintain and reestablish a non-pathogenic, natural or genetically modified intra-vaginal bacterial flora.

SUMMARY OF THE INVENTION

It is an object of the present invention to provide a condom coated with lactic acid bacteria contained composition having the effect of healthy bacteria establishment, maintenance and reestablishment.

It is another object of the present invention to provide a method for the manufacture of a condom coated with lactic acid bacteria contained compositions.

Lactic acid bacteria contained compositions having the multi-beneficial action used in the present invention can be used as a powder form or micro-encapsulated form thereof and can be a composite form combined with other components such as a lubricant.

When the micro-encapsulated form has been used, the viable lactic acid bacteria are micro-encapsulated, which can maintain the viability of the lactic acid bacteria and also protect the viable lactic acid bacteria from the action of the antimicrobial or the other compositions during the "shelf-life" of the condom presented in the invention. The coating or substance which encapsulates the bacteria on the other hand is of such material which releases the bacteria in the vaginal milieu primarily due to the effect of moisture. The released lactic acid bacteria serve to maintain or reestablish the healthy flora on the vaginal mucosa, and excrete hydrogen peroxide and other bactericidins which suppress pathogenic microbial that promote infections.

The lactic acid bacteria of the lactic acid bacteria contained compositions having the multi-beneficial action of the present invention can be natural or genetically modified acidophilic bacteria, bifidobacteria, the species *Lactococcus lactis, Lactobacillus rhamnosus, Lactobacillus fermentum, Lactobacillus brevis, Lactobacillus plantarum, Lactobacillus casei, Lactobacillus delbruckii* sbp. *bulgaricus, Lactobacillus delbruckii* sbp. *lactis, Streptococcus thermophilus, Streptococcus gordonii* or *Leuconostoc mesenteroides*.

BRIEF DESCRIPTION OF THE DRAWINGS

The drawings disclose an illustrative embodiment of the present invention which serves to exemplify the various advantages and objects hereof, and are as follows.

DETAILED DESCRIPTION OF THE PREFERRED EMBODIMENT

Figure 1:
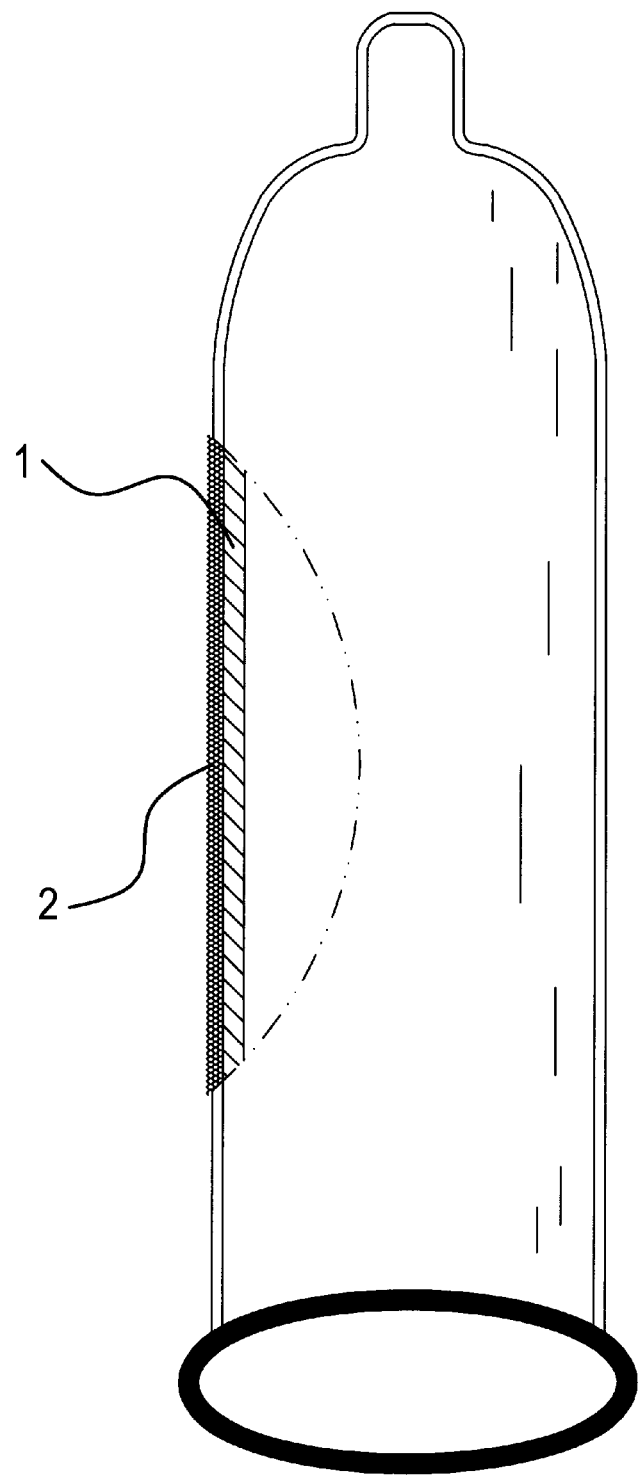
FIG. 1 is a diagrammatic representation of a condom, partially cut-away, showing a coating of lactic acid bacteria contained compositions on the outside.

The present invention is a condom providing contraceptive effect, sexually transmitted disease prevention and vaginal healthy improvement, which is coated with compositions containing viable lactic acid bacteria. The bacteria are prepared in powder form or micro-encapsulated to protect them from the action of other antimicrobial agent. Additionally, all the lactic acid bacteria used in the present invention can be purchased from commercial sources, or can be obtained from laboratory strains, and the lactic acid bacteria using in this present invention can be natural or genetically modified species.

The viable lactic acid bacteria is the essential component of the condom of this present invention, which can be acidophilic bacteria, bifidobacteria, the species *Lactococcus lactis, Lactobacillus rhamnosus, Lactobacillus fermentum, Lactobacillus brevis, Lactobacillus plantarum, Lactobacillus casei, Lactobacillus delbruckii* sbp. *bulgaricus, Lactobacillus delbruckii* sbp. *lactis, Streptococcus thermophilus, Streptococcus gordonii* or *Leuconostoc mesenteroides*, and should be present at least in the range of $10^3$ viable bacteria per condom, a more preferred range being $10^5$ to $10^7$, and the preferred number of viable bacteria being approximately 1 million ($10^6$) per condom. As is know in the prior art, all the lactic acid bacteria mentioned above are "friendly" bacteria, and form the healthy flora in the human body. Some of these bacteria are known to produce certain bactericidins and hydrogen peroxide, which helps to suppress pathogenic bacteria, called the probiotic lactic acid bacteria. The probiotic lactic acid bacteria are, to this effect, of particular interest within the framework of the present invention. These bacteria are in fact capable of adhering to human vaginal mucosa, of excluding pathogenic bacteria on human vaginal mucosa, and/or of acting on the human immune system by allowing it to react more strongly to external aggression (immunomodulatory capacity).

Additionally, the lactic acid bacteria of the lactic acid bacteria contained compositions can be freeze-dried and micro-encapsulated in the separation substance comprising solidified fatty acid, sodium alginate, polymerized hydroxypropylmethylcellulose, polymerized polyvinylpyrrolidone, or mixtures thereof, in order to protect them from the action of other antimicrobial agent, such as nonoxynol 9.

In addition to the lactic acid bacteria contained compositions, the condom of the present invention also coated with the compositions containing the lactic acid bacteria contained composition as a component with the non-essential ingredients or components, such as spermicidal and bactericidal agent or agents. These components are considered non-essential because the basic objectives of the invention can be attained without them. Nevertheless, the embodiments of the invention which include these non-essential components offer certain advantages, and are therefore considered the preferred embodiments, and should also be considered novel and innovation, in their combination, to the basic embodiments.

A method of coating lactic acid bacteria contained compositions on a condom, if necessary, comprises coating the whole surface or necessary portion of a condom by dropping, dipping, coating or spraying a solution containing a lubricant as described before. In this way, a condom having healthy bacteria establish, maintained and reestablish effect plus with a lubricating effect can be obtained.

On a condom manufactured in a usual method, for example, a condom which is stripped off from a condom-former and rolled up after the forming process followed by examination process, a composition containing lactic acid bacteria is added and the condom is packaged with film to be spread with lactic acid bacteria contained composition on the whole surface thereof. As a healthy component, a powder form lactic acid bacteria contained composition added with a lubricant as described before can be used. In this way, a wet-type of product coated with a multi-beneficial effect in a creamy state can be obtained.

In another method, a condom can be taken from a water vessel (pinhole examination vessel) remaining on the condom former as described before, dipped in a dipping vessel (liquid vat) containing a solution of the composition which comprises lactic acid bacteria having multi-beneficial effect to be coated with lactic acid bacteria contained composition on the whole surface thereof, taken from the dipping vessel, dried, stripped off from the former and rolled up.

A solution of lactic acid bacteria contained composition to a dipping vessel can be an gelled solution of lactic acid bacteria contained composition together with a lubricant, for example, isopropyl alcohol, as described before. In this way, a dried product coated with a multi-beneficial agent can be obtained.

In addition, on a condom, produced like this silicone oil or an aqueous solution of a lubricant can be added, followed by film packaging thereof.

The present invention is further explained by the following examples, but these examples are illustrated to exemplify the present invention and the scope of the present invention is not restricted by these examples.

EXAMPLES

Lactic Acid Bacteria Preperation

At first, a concrete example of preparation of lactic acid bacteria contained compositions used in the present invention is exemplified. The lactic acid bacteria of the present invention can be grown in any medium which provides effective growth of the microbe without contamination, loss of genetic stability, or loss of any other desirable characteristics of the lactic acid bacteria strains. More particularly, the lactic acid bacteria strains of the present invention are grown in a culture medium which includes a source of assimilable organic carbon, a source of assimilable nitrogen and appropriate salts and trace metals. A preferred medium for culturing *Lactobacillus* strains of the present invention is MRS medium.

The lactic acid bacteria microorganisms of the present invention can be cultured in conventional culture conditions, which include, but are not limited to agar surface culture or broth fermentation. Both agar surface culture and broth fermentation methods are well known in the art. The *Lactobacillus* are preferably cultured anaerobically or microaerophilically.

The temperature of the culture medium can be any temperature suitable for growth of the lactic acid bacteria strains. For example, prior to inoculation of the culture medium with an inoculum, the culture medium can be brought to and maintained at a temperature in the range of about 20° C.–35° C., and more preferably about 25° C.–35° C.

The culture medium is inoculated with an actively growing culture of the lactic acid bacteria strains of the present invention in an amount sufficient to produce, after a reasonable growth period, a suitable cell density for transfer to the next drying process, such as freeze drying or spay drying, which is in order to remove the medium. Typical inoculation cell densities are within the range of about $10^6$–$10^9$ CFUs/ml, and more preferably about $10^8$–$10^9$ CFUs/ml, based on the dry weight of the cells. The cells are then grown to a cell density in the range of about $10^7$–$10^9$ CFUs/ml, and more preferably to about $10^8$ CFUs/ml. At this stage, the cells are harvested for the next drying and lyophilized process.

Encapsulation Method

Viable, lyophilized lactic acid bacteria that have been lyophilized after the removal of the media are used for encapsulation. The bacteria can be obtained from commercial sources, or can be obtained from laboratory strains. The organisms are grown to log phase in nutrient media. Suitable media include Thayer-Martin media, Trypticase Soy, Brain-Heart Infusion Broth, or any other enriched media suitable for the cultivation of these organisms, as no particular media is critical to the success of this suppository. The only important factors are the viability and quantity of the microorganisms that are always determined by standard clinical laboratory dilution methods, such as plating the quantified dilution of bacteria on to blood agar plates or other enriched media, incubating at 37° C. for 24–48 hours in a 5–10% carbon dioxide atmosphere, and then performing a colony count. The removal of the nutrient media is done by centrifugation at 14,000.times.g at 0–4° C., and then washing with sterile, balanced salts and 5% glucose solution at least three times after the initial centrifugation. The bacteria are then "snap frozen" with liquid nitrogen and then lyophilized under high vacuum.

The freshly obtained, washed and lyophilized bacteria obtained as described above are suspended in 10 ml of 5% glucose saline solution in such volume so as to obtain a heavy suspension of bacteria which contains between one to ten billion organisms per ml, at 0–4° C. All of these procedures are performed in the 0–4° C. temperature range unless otherwise noted, in order to maintain viability of the lactobacilli bacteria which at room temperature lose viability. The suspension of bacteria is rapidly, but gently, stirred while 0.2–0.4 ml of sodium alginate solution (1.5% weight by volume) is added. The above mixture is then transferred into a 4 liter round bottom flask by using a nitrogen stream through a sheathed 14 gauge needle. The 4 liter round bottom flask was previously washed with a 5% albumin solution, and thereafter heated for at least 10 hours at 65° C., and the needle and the tubing used in the process have also been treated this way.

Thereafter the above mixture is forced through a 30 gauge multi-beveled needle under pressure using a large syringe and nitrogen stream. Very small droplets are generated at the end of the needle which are dried by the nitrogen and air stream around the 30 gauge needle, and the droplets are collected in an aqueous solution of 1.3–2% calcium chloride where they gel. Thereafter, they are washed at least three times with 0.08–0.13% 2-(N-cyclohexyl-amino) ethanesulfonic acid (CHES) solution and 1.0–1.5% calcium chloride solution.

The gelled droplets or little spheres are further washed with at least a five fold excess of the 0.1% CHES 1.1% calcium chloride, and normal saline solution. The resultant spheres are then "snap frozen" in liquid nitrogen and then lyophilized. After these steps, the encapsulated organisms can be used in the formulations of the present invention.

As an improvement over encapsulation method mentioned above, the following further steps are performed to render the bacteria more resistant to the cationic antimicrobials. The steps are performed at 0–4° C. Thus, after the washings described in encapsulation method mentioned above, the materials are reacted with poly L-lysine (Sigma) solution (0.05% w/v) spheres for ten minutes. The spheres are then washed with normal saline buffered to pH 4.5 with lactic acid. The resultant spheres are then "snap frozen" in liquid nitrogen and then lyophilized. After these steps, the encapsulated organisms can be used in the formulations of the present invention.

Condom Coating

Example 1

The lactic acid bacteria contained compositions was coated on a condom which was formed, examined, stripped off and rolled up, followed by heat-sealing thereof. Then these compositions gradually permeated and spread over the whole surface of the condom and a coated condom with wet and suitable lubricating properties was obtained.

Example 2

An aqueous solution of .lambda.-carrageenan mixed with isopropyl alcohol was put in a liquid vat and a condom (while still covering a condom-former) was dipped therein after the examination for pinholes.

The condom was taken from the liquid vat, dried, stripped off from the former and rolled up. In this way a condom coated homogenously with the lactic acid bacteria contained compositions was obtained.

Example 3

An aqueous solution of a lubricant consisting of propylene glycol, sodium alginate and glycerine was coated on the condom obtained in example 2, followed by heat-sealing to make the condom coated homogeneously with the lactic acid bacteria contained compositions and further with a lubricant.

The drawings disclose an illustrative embodiment of the present invention.

FIG. 1 is an illustration, in partial cross-section, of a condom 1 coated on the outside with a layer 2 comprising a mixture of lubricant and the lactic acid bacteria contained compositions.

Figure 2:
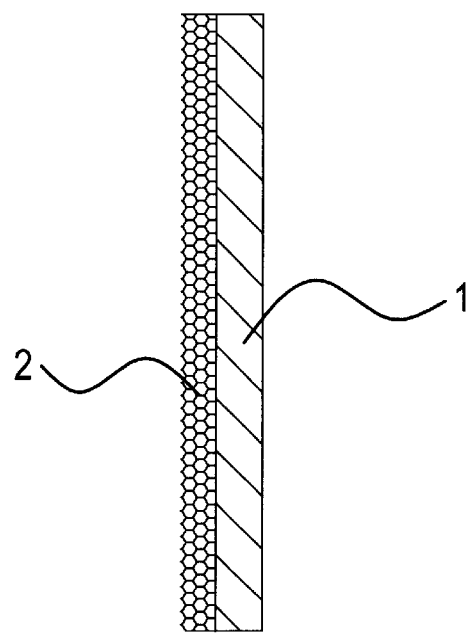
FIG. 2 is a cross-section of a portion of the coated condom of FIG. 1.

FIG. 2 is a cross-section of a portion of a condom 1 coated with a layer 2 comprising the lactic acid bacteria contained compositions. The coating is thinner than the condom 1.

Figure 3:
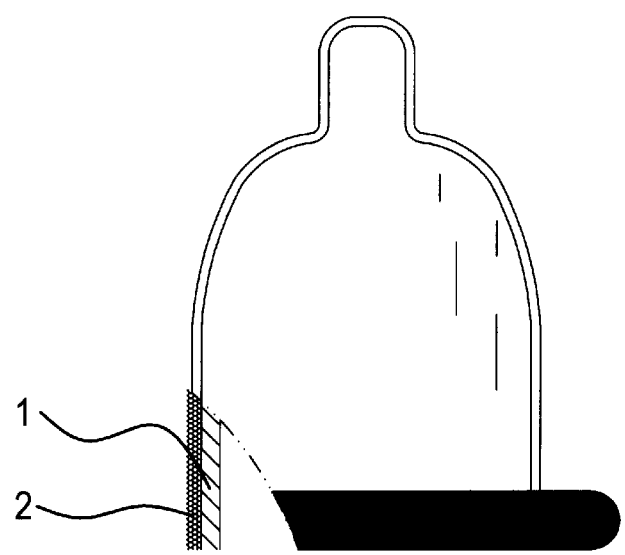
FIG. 3 is a diagrammatic representation, partially cut-away, of a rolled condom of FIG. 1.

FIG. 3 is an illustration, in partial cross-section, of a rolled condom 1 coated on the outside with a layer comprising a mixture of lubricant and the lactic acid bacteria contained compositions.

Figure 4:
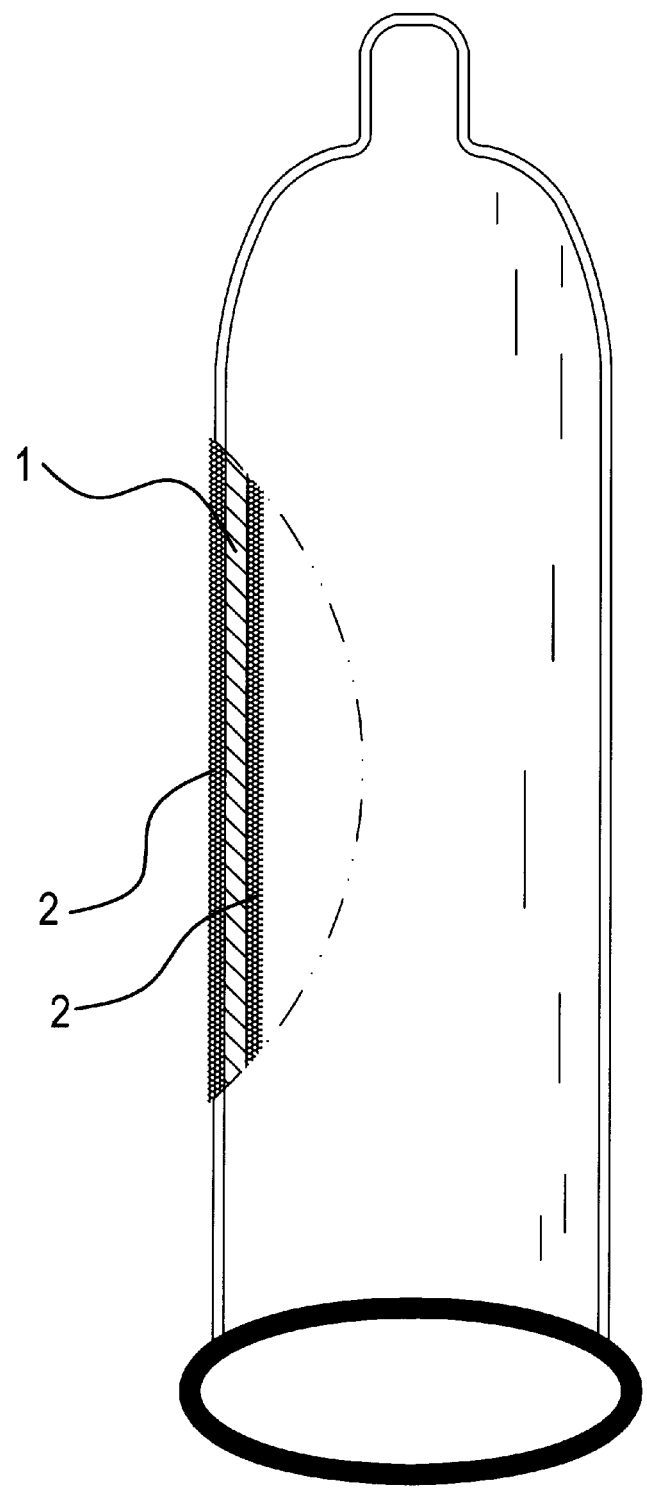
FIG. 4 is a diagrammatic representation, partially cut-away, of a condom having a coating of lactic acid contained compositions on the inside and the outside.

FIG. 4 is an illustration in partial cross-section of a condom 1 coated with a layer 2 comprising the lactic acid bacteria contained compositions, on the inside and the outside of the condom.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A condom for establishing, maintaining and reestablishing intra-vaginal bacterial flora, characterized in that said condom is coated with a lactic acid bacteria contained composition comprising at least $10^3$ viable lactic acid bacteria.

2. The condom of claim 1 wherein said condom is male condom or female condom.

3. The condom of claim 1 wherein said lactic acid bacteria are natural lactic acid bacteria.

4. The condom of claim 1 wherein said lactic acid bacteria are genetically modified lactic acid bacteria.

5. The condom of claim 1 wherein said lactic acid bacteria is selected from a group consisting of acidophilic bacteria, bifidobacteria, *Lactococcus lactis, Lactobacillus rhamnosus, Lactobacillus fermentum, Lactobacillus brevis, Lactobacillus plantarum, Lactobacillus casei, Lactobacillus delbruckii* sbp. *bulgaricus, Lactobacillus delbruckii* sbp. *lactis, Streptococcus thermophilus, Streptococcus gordonii, Leuconostoc mesenteroides* and mixtures thereof.

6. The condom of claim 1 wherein said lactic acid bacteria contained composition comprises at least one species of said lactic acid bacteria.

7. The condom of claim 1 wherein said lactic acid bacteria adheres to human vaginal cells, thereby inhibiting adhesion to said human vaginal cells by pathogenic microbial and virus or acting on the human immune system.

8. The condom of claim 1 wherein said composition is a solution.

9. The condom of claim 1 wherein said composition is a solid.

10. The condom of claim 1 wherein said composition is a lubricant.

11. The condom of claim 1 wherein said composition comprising powder form lactic acid bacteria.

12. The condom of claim 1 wherein said composition comprising encapsulated lactic acid bacteria.

13. The condom of claim 12 wherein said encapsulated lactic acid bacteria are micro-encapsulated in a separation substance selected from a group consisting of solidified fatty acid, sodium alginate, polymerized hydroxypropylmethylcellulose, polymerized polyvinylpyrrolidone, and mixtures thereof.

14. A method of manufacturing a condom coated with lactic acid bacteria, comprising steps of:

forming a condom and examining the quality thereof;

stripping off said condom from a former and rolling up said condom; and dropping a lactic acid bacteria contained composition on said condom and followed by packaging to homogeneously coat said condom with said composition.

15. A method of manufacturing a condom coated with lactic acid bacteria, comprising steps of:
   forming a condom and examining the quality thereof;
   dipping said condom which covers a former into a lactic acid bacteria contained composition;
   coating said condom homogeneously with said lactic acid bacteria contained composition; and
   drying said condom and then striping it off from said former and rolling it up.

16. The method of claim 15 further comprising a step of adding a hydrophilic or hydrophobic substance to said condom to provide a lubricating effect.

* * * * *